United States Patent [19]

Buzza et al.

[11] 4,003,705
[45] Jan. 18, 1977

[54] ANALYSIS APPARATUS AND METHOD OF MEASURING RATE OF CHANGE OF ELECTROLYTE pH

[75] Inventors: Edmund E. Buzza; James C. Sternberg, both of Fullerton, Calif.

[73] Assignee: Beckman Instruments, Inc., Fullerton, Calif.

[22] Filed: June 12, 1975

[21] Appl. No.: 586,435

[52] U.S. Cl. .......................... 23/230 R; 23/230 B; 23/253 R; 204/195 B; 204/195 P; 204/195 T

[51] Int. Cl.² .............. G01N 27/26; G01N 31/16; G01N 33/16

[58] Field of Search ......... 23/230 B, 253 R, 230 R; 204/1 B, 1 K, 1 M, 1 H, 195 B, 195 P, 195 T

[56] References Cited
UNITED STATES PATENTS

| | | | |
|---|---|---|---|
| 2,878,106 | 3/1959 | Malmstadt | 23/253 R |
| 3,503,861 | 3/1970 | Volpe | 204/195 P |
| 3,510,421 | 5/1970 | Gealt | 204/195 P |
| 3,551,109 | 12/1970 | Dahms | 23/230 B |
| 3,577,332 | 5/1971 | Porter et al. | 204/195 P |
| 3,638,109 | 1/1972 | Harnoncourt | 23/230 B X |
| 3,707,455 | 12/1972 | Derr et al. | 204/195 P |
| 3,709,796 | 1/1973 | King et al. | 204/195 G X |
| 3,767,552 | 10/1973 | Lauer | 204/195 P |
| 3,769,178 | 10/1973 | Rothermel, Jr. | 23/253 R X |
| 3,912,613 | 10/1975 | Heuser | 204/195 T X |

Primary Examiner—Joseph Scovronek
Attorney, Agent, or Firm—R. J. Steinmeyer; R. R. Meads

[57] ABSTRACT

Apparatus for measuring carbon dioxide and chloride in blood. A blood sample is reacted with acid in a sample container to release carbon dioxide, a portion of which diffuses through a gas-permeable membrane and reacts with an electrolyte to change the pH thereof. A pair of pH measuring electrodes monitor the electrolyte pH at respective locations adjacent to and remote from the region of reaction within the electrolyte. The pH electrodes are coupled to respective input terminals of a differential amplifier to derive a differential pH signal. The differential pH signal is differentiated to derive a rate of change of pH output signal which is measured to indicate the concentration of carbon dioxide. The pH measuring electrodes are in electrolytic communication and means is provided to renew the electrolyte between measurements. Coulometric measurement of chloride in the sample is performed simultaneously with the carbon dioxide measurement.

21 Claims, 6 Drawing Figures

ANALYSIS APPARATUS AND METHOD OF MEASURING RATE OF CHANGE OF ELECTROLYTE PH

BACKGROUND OF THE INVENTION

1. Field of the Invention

The present invention relates generally to electrochemical analysis apparatus and, more particularly, to an analyzer capable of automatically and directly analyzing biological and biochemical substances found, for example, in blood serum.

2. Description of the Prior Art

A variety of techniques and apparatus have been developed in the past for analyzing small blood samples for the presence of bicarbonate, chloride, and other constituents. The use of these measurements is well known to physicians and other clinical and diagnostic specialists for applications in surgery, pulmonary function studies, cardiac catheterization, anesthesia, as well as in other related fields.

Serum bicarbonate, which is present in human blood at about 30 milliequivalents per liter, has been measured by a variety of methods all of which involve acidifying the blood sample to release carbon dioxide. These methods include back titration with a base of the remaining excess of a known amount of acid added to a blood sample; colorimetric measurement of the carbon dioxide which diffuses from the sample solution across a dialysis membrane into a basic solution containing an acid-base indicator; colorimetric measurement of the carbon dioxide swept out of the sample solution into a basic scrubbing solution containing an acid-base indicator; gasometric measurement of the volume of carbon dioxide released from the sample; and calculation of the carbon dioxide in the sample using a conventional $pCO_2$ electrode to measure the partial pressure of carbon dioxide and a pH electrode to measure the pH of the sample.

While the above methods generally will provide some measure of bicarbonate, they have not proven satisfactory in many respects. Back titration with base of the acid excess in an indirect measurement technique performed after the carbon dioxide has been released to the atompshere. Being indirect, the method is less accurate than methods employing direct measurement of the carbon dioxide actually released. Moreover, titration must proceed to its end point before a measurement is available.

Colorimetric measurements of carbon dioxide released from the sample are time consuming and complex. It is difficult to sweep out and to adsorb the carbon dioxide released. The reactions involved must proceed to equilibrium over a prolonged period, and thus such methods are unsatisfactory for providing rapid and reliable sample measurements.

Gasometric measurement of the carbon dioxide released is also slow and, moreover, requires highly trained operators for proper execution.

Conventional $pCO_2$ electrodes are inherently slow to equilibrate after exposure to carbon dioxide, and therefore such electrodes are generally unsuited to the automatic and rapid analysis of samples. The equilibration process must generally be permitted to occur twice for each measurement, once with the $CO_2$ containing sample, and once again with the fresh reagent prior to sample introduction.

In view of the foregoing, it is apparent that a need exists for analysis apparatus for performing blood chemistry analysis and the like which can provide rapid and accurate measurements with minimal operator intervention and with a minimum level of required operator skill. The apparatus should overcome the disadvantages of the bicarbonate measuring methods enumerated above and should preferably do so in a manner which further enables simultaneous measurement of other constitutents, such as chloride, of the same sample.

SUMMARY OF THE INVENTION

The present invention resides in a new and improved analysis apparatus and method for analyzing biological and biochemical samples, such as blood, which has the capability of directly, rapidly, and accurately measuring the sample's carbon dioxide content. Moreover, the apparatus overcomes the disadvantages of the prior approaches and achieves such improved results in a commerically practical form that is relatively simple in construction, reliable in operation, and straightforward to operate. In addition, the apparatus is capable of simultaneously measuring chloride content of the same sample.

In accordance with a primary aspect of the invention, sensor means is provided for monitoring a chemically reactable substance to be analyzed and the sensor means includes an electrolyte which undergoes a change in pH with time when reacted with the substance. The invention further comprises means coupled to the sensor means for generating an output signal proportional to the instantaneous time rate of change of pH of the solution, and means for measuring the output signal to determine the concentration of the substance in the electrolyte.

The sensor means of the invention may include a pH measuring electrode mounted in a sample cup and communicating with the sample through a gas-permeable but ion-impermeable membrane. Injection of sample into the sample cup and into a reagent contained therein produces the aforementioned chemically reactable substance which diffuses through the membrane and changes the electrolyte pH. A second pH measuring electrode is in electrolytic communication with the first pH measuring electrode but remote therefrom. Means are provided to circulate fresh electrolyte past both measuring electrodes between measurements to provide rapid equilibration of the electrodes.

The two pH electrodes are coupled to the input terminals of a differential amplifier and differential pH signal is derived at the amplifier output terminal which is insensitive to drift and temperature variations. The pH signal is, in turn, differentiated to derive the output signal proportional to the instantaneous time rate of change of pH.

In accordance with a further aspect of the invention, coulometric determination of chloride of the same sample is performed simultaneously with the carbon dioxide determination.

DESCRIPTION OF THE PREFERRED EMBODIMENT

Figure 1:
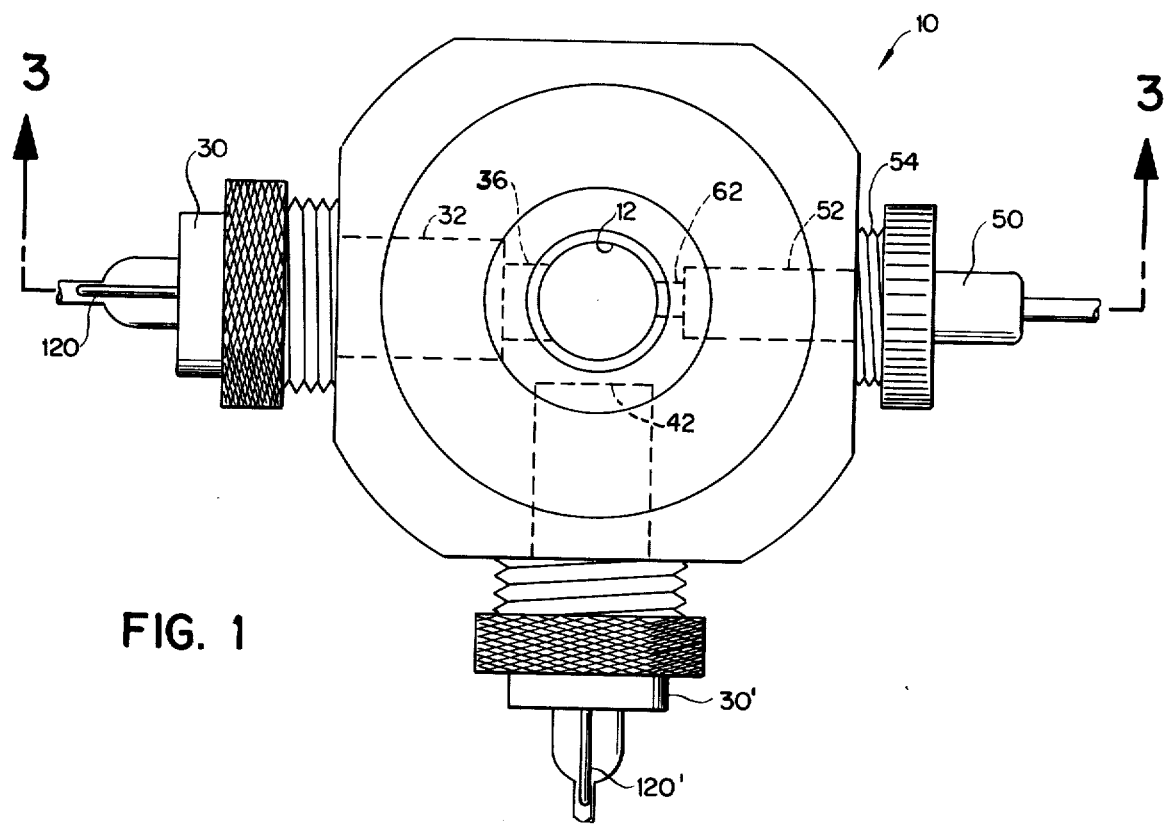
FIG. 1 is a top plan view of a sample cup employed in the analysis apparatus of the invention and illustrates the mounting of the bicarbonate and chloride determining electrodes of the invention.
Figure 2:
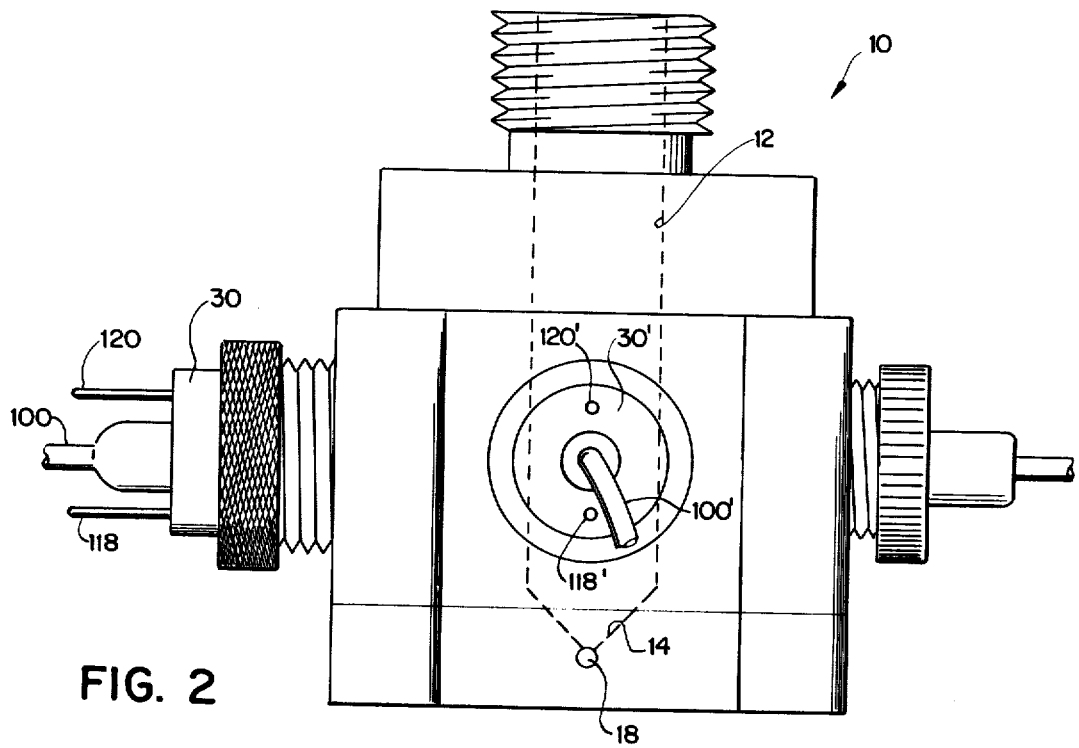
FIG. 2 is a front elevational view of the sample cup and electrode structures of FIG. 1.
Figure 3:
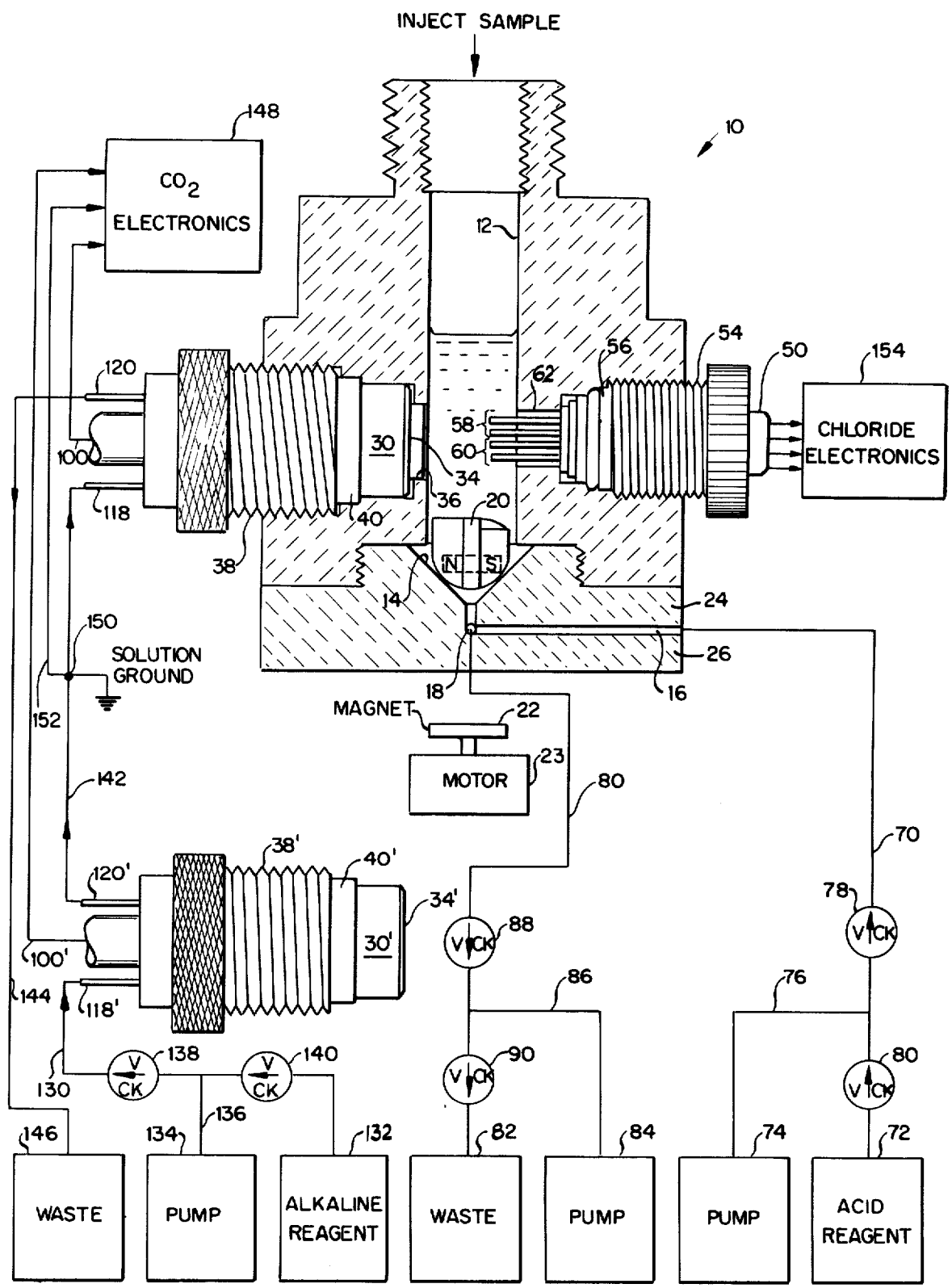
FIG. 3 is a longitudinal sectional view, taken in a generally vertical plane along line 3—3 in FIG. 1. The figure illustrates diagrammatically the flow of acid and alkaline reagents in the apparatus.

As shown in the drawings for purposes of illustration, and in particular FIGS. 1–3 thereof, the apparatus of the invention embodies an analysis cell 10 formed from a block of insulating material such as polymethylmethacrylate. A cylindrical vertically extending chamber 12, open at its upper end, is formed in the block. The samples to be analyzed may be injected into the chamber through the upper end thereof by means of a microsampling device such as a pipette or burette in a conventional manner. The lower surface 14 of the chamber is conically configured. A pair of passages 16 and 18 lie in a generally horizontal plane in the block and intersect one another at a right angle at the apex of the conical lower surface of the chamber. Reagent is supplied to and drained from the chamber through these passages. A conventional magnetic stirring element 20 is positioned in the chamber and is adapted to be rotated by a magnet 22 positioned below the cell 10 and rotated by means of a motor 24. If desired, the block of the analysis cell 10 may be formed from two mating parts 25 and 26 threaded together as shown in FIG. 3.

For the measurement of carbon dioxide content and chloride in blood, three measuring sensors are mounted in horizontal bores in the wall of the analysis cell 10. A first $CO_2$ measuring sensor 30 is mounted in a first horizontal bore 32 and has a sensing end 34 communicating with the sample chamber 12 through a reduced diameter portion 36 of bore 32. Sensor 30 is retained with the bore 32 by a cylindrical member 38 threaded into bore 32 and bearing against an annular shoulder 40 on the sensor.

A second $CO_2$ measuring sensor 30', which may be identical to sensor 30, is mounted in a second horizontal bore 42. As best illustrated in FIG. 1, bore 42 is a blind bore which does not communicate with the reaction chamber 12. The second $CO_2$ measuring sensor 30' therefore has sensed end 34' isolated from the reaction chamber. Sensor 30' is retained within blind bore 42 by a second cylindrical member 38' threaded into the bore and bearing against an annular shoulder 40' on the sensor. $CO_2$ measuring sensors 30 and 30' are employed in the measurement of carbon dioxide content in a manner discussed later.

The third measuring sensor 50 is mounted in a third horizontal bore 52 and is retained therein by a cylindrical member 54 threaded into the bore and bearing against an annular shoulder 56 of the electrode module. The sensor includes two pairs of electrodes 58 and 60 which extend into the reaction chamber 16 through a reduced diameter portion 62 of bore 52. Electrode module 50 is employed in the measurement of chloride in a manner discussed later.

A conduit 70 connects passage 16 in analysis cell 10 to a reservoir 72 containing a suitable reagent, such as dilute sulfuric acid. A pump 74, preferably of a conventional syringe type, is provided for withdrawing reagent from the reservoir 72 and for delivering the same through passage 16 into the reaction chamber 12. Pump 74 is connected to conduit 70 by means of conduit 76 between a pair of valves 78 and 80. Valve 80 is arranged to permit withdrawal of a measured amount of reagent from the reservoir 72 but to prevent the delivery of liquid thereto. The valve 78 is arranged to permit the delivery of the measured amount of reagent through conduit 70 into the chamber 16 but to prevent the withdrawal of liquid from the chamber through the conduit. This pair of valves may be combined into a single component, if desired.

In order to drain liquid from the reaction chamber 12, a conduit 80 connects passage 18 in the cell 10 to a waste reservoir 82. A pump 84, which may be identical in construction to pump 74, is connected to conduit 80 by means of conduit 86 between a pair of valves 88 and 90. Valve 88 is arranged to permit flow through conduit 80 from the chamber 12 into the conduit 86 and to prevent flow in the opposite direction through conduit 80. Valve 90 permits flow of liquid into the waste reservoir 82 but prevents withdrawal of waste from the reservoir. This pair of valves may be combined into a single component if desired.

Figure 4:
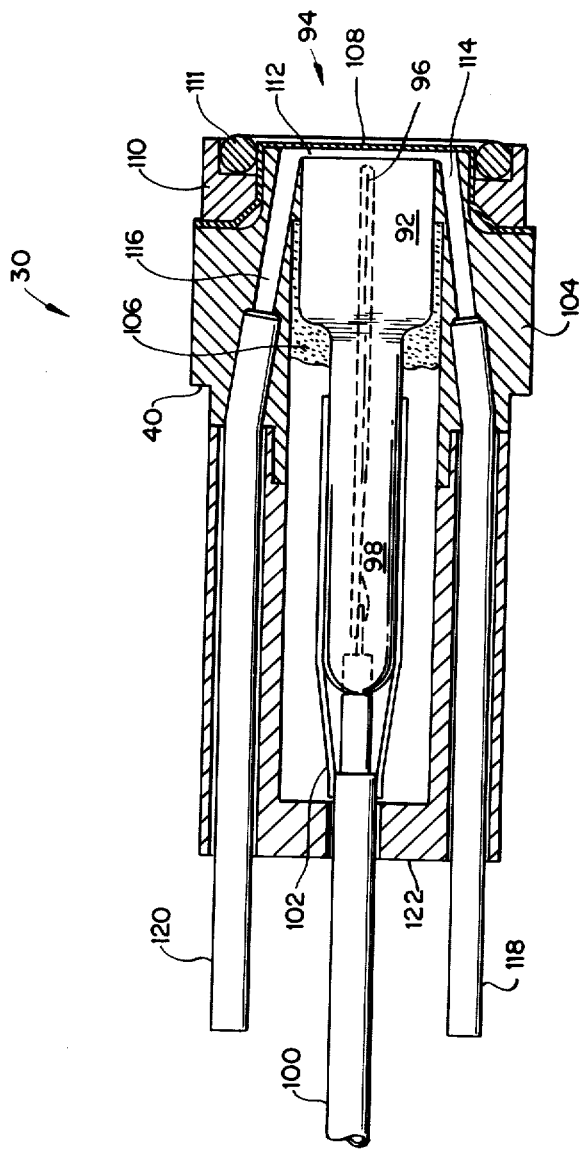
FIG. 4 is a cross-sectional view through a pH cell of the invention.

FIG. 4 illustrates a $CO_2$ measuring sensor 30 or 30' of the invention including a glass pH measuring electrode 92. The pH electrode has a flat sensing end 94 and may comprise a conventional silver-silver chloride half cell 96 positioned within a chamber filled with an electrolyte solution. Electical connection is made to the half cell at the end of the electrode remote from sensing end 94. Cable 100 having a conductor therein (not shown) surrounded by a shield 102 is joined to the half cell and the end 98 of the electrode is fused to the center conductor of cable 100. Further shielding of the electrode may be provided by a conductive shrink tube surrounding the joint between cable 100 and surrounding the upper portion of the electrode.

The housing for the pH electrode 92 includes a cylindrical member 104 coaxially disposed around electrode 92 and having an open end adjacent the sensing end 94 of the electrode. Electrode 92 is held in place within member 104 by means of an epoxy adhesive 106. A gas permeable, ion impermeable membrane 108 is disposed over the open end of the cylindrical member 104 and is held in place by a retaining ring 110 which frictionally engages the end of the cylindrical member with the perimeter of the membrane trapped securely between the retaining ring and the cylindrical member. Suitable materials for membrane 108 are silicone rubber, polyethylene, or polytetrafluoroethylene. The cylindrical member 104 provides the annular shoulder 40 engaged by threaded member 38 to mount the measuring sensor within the horizontal bore of the reaction cell 10. An O-ring 111 is seated within a recess in the retaining spring 110 for seating and sealing the measuring cell within the horizontal bore.

An electrolyte film space of about 5 thousandths of an inch 112 is defined between the sensing end 94 of electrode 92 and the membrane 108. Electrolyte communication with the film space 112 is provided by first and second passages 114 and 116 extending generally axially in cylindrical member 104. Passages 114 and 116 are inclined slightly so as to communicate with the electrolyte space 112 through the interior wall of cylindrical member 104 and are connected to stainless steel tubes 118 and 120, respectively. The innermost ends of tubes 118 and 120 are secured within cylindrical member 104 by means of an epoxy adhesive while outer exposed ends of the tubes extend axially through bores in a cylindrical wall of a cap having a closed end 122 through which cable 100 extends. The outer ends of the tubes are connected to an electrolyte supply. For example, tube 118 may function as an inlet tube to receive electrolyte from a reservoir for delivery to electrolyte film space 112 while tube 120 would function as an outlet tube to deliver electrolyte from the film space to waste. Dimensions of tubes 118 and 120 may be 1.25 in. in length with an inside diameter of 0.047 and an outside diameter of 0.065 in.

In practice, the spacing between the membrane 108 and the sensing end 94 of electrode 92 may be on the order of 0.005 inches. Because of this minute electrolyte space, the electrolyte therein and the measuring electrode are extremely sensitive to a gas, for example carbon dioxide, which diffuses through membrane 108 into the electrolyte space during operation of the sensor 30 to detect and measure the carbon dioxide content in a blood sample injected into the analysis cell 10.

More particularly, and with reference to FIG. 3, apparatus of the invention for measuring the carbon dioxide content of a blood sample includes the $CO_2$ measuring sensors 30' and 30, both of which may have the structural configuration illustrated in FIG. 4. An electrolyte flow path through both $CO_2$ measuring sensors is provided in the following manner. A conduit 130 connects inlet tube 118' of sensor 30' to a reservoir 132 containing a suitable electrolyte such as potassium bicarbonate. A pump 134, which may be similar to pumps 74 and 84, is provided for withdrawing electrolyte from the reservoir 132 and for delivering the same through inlet tube 118' into the electrolyte space of $CO_2$ measuring sensor 30'. Pump 134 is connected to conduit 130 by a conduit 136 between a pair of valves 138 and 140. Valve 140 is arranged to permit withdrawal of a measured amount of electrolyte from the reservoir 132 but to prevent delivery of liquid thereto. The valve 138 is arranged to permit the delivery of the measured amount of electrolyte through conduit 130 into the $CO_2$ measuring sensor 30' but to prevent the withdrawal of liquid from the measuring sensor through the conduit. Again, the pair of valves may be combined into a single component, if desired.

Outlet tube 120' of sensor 30' is connected by conduit 142 to inlet tube 118 of measuring sensor 30 to provide electrolytic communication between the two pH electrodes. The outlet tube 120 of sensor 30 is connected by a conduit 144 to a waste reservoir 146, the waste reservoir being separate from waste reservoir 82. Pump 134 thereby delivers a measured amount of electrolyte from reservoir 132 along a series flow path through measuring sensors 30' and 30 to waste reservoir 146.

Electrical output signals from each of the pH electrodes 92 and 92' are supplied over respective cables 100' and 100 to electronic circuitry identified by numeral 148. An electrolyte grounding connection 150 is made in conduit 142 and this ground level is supplied over conductor 152 to circuitry 148.

Figure 5:
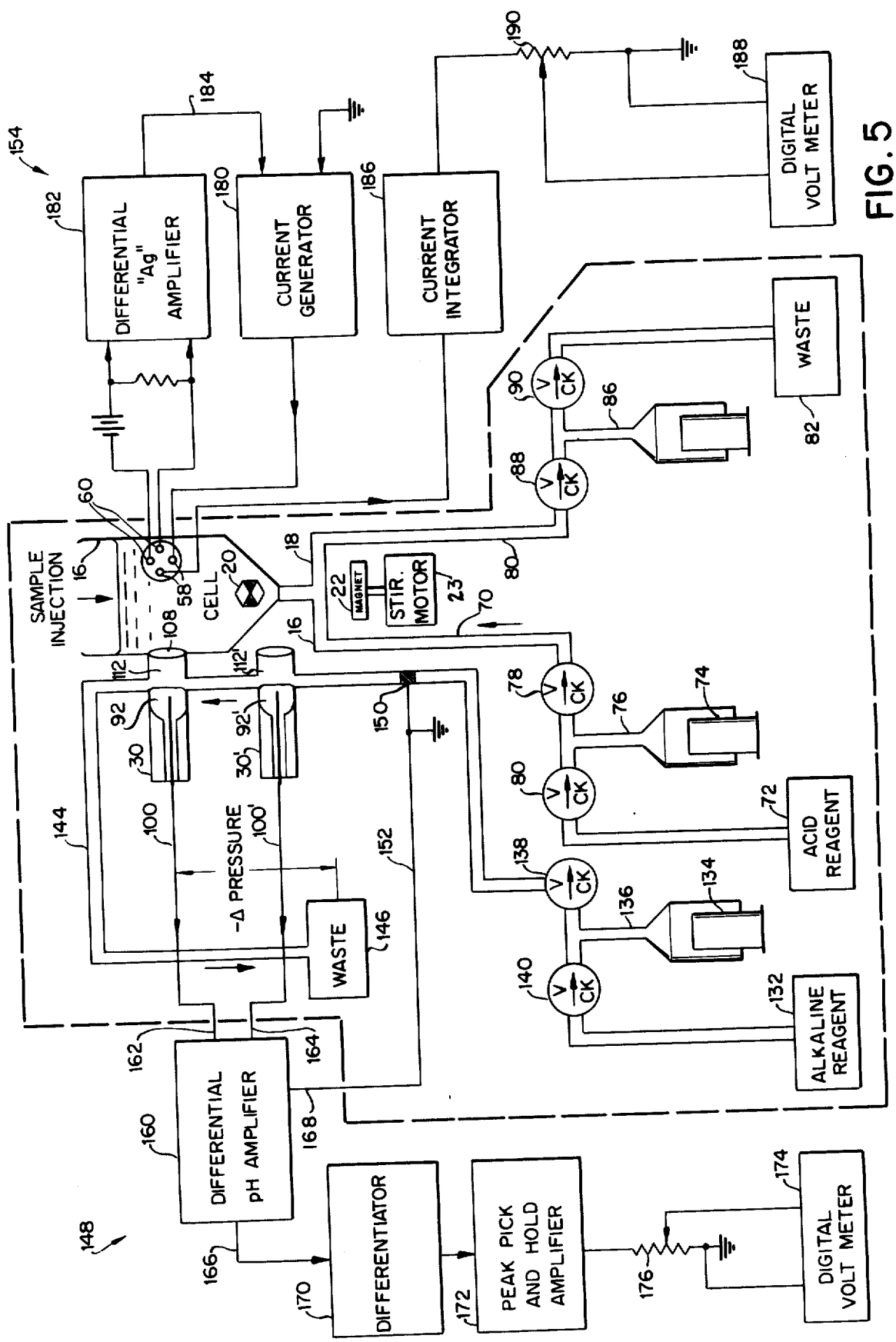
FIG. 5 is a combined diagrammatic and electrical schematic diagram of the analysis apparatus of the invention.

The principle of sample carbon dioxide content measurement will be discussed with reference to FIG. 5 which illustrates certain structural features of FIG. 4 in diagrammatic form and shows in more detail the electronic circuits 148 and 154 of FIG. 4. The numerals employed in FIGS. 1–4 have been used to identify the same features in FIG. 5.

When a blood sample containing dissolved carbon dioxide and bicarbonate is injected into reaction chamber 12, the bicarbonate in the sample is decomposed by the action of the sulfuric acid reagent within the chamber in accordance with the following equation:

A proportional part of the total carbon dioxide (original carbon dioxide plus that generated from bicarbonate) diffuses through gas permeable membrane 108 and $CO_2$ measuring sensor 30. The bicarbonate electrolyte within the electrolyte space 112 of the measuring cell has a constant pH since it is in equilibrium with the partial pressure of carbon dioxide in the atmosphere in accordance with the following equation:

The carbon dioxide which diffuses through membrane 108 lowers the pH of the bicarbonate electrolyte. Applications have discovered that the rate of change of this pH can be measured to determine the concentration of bicarbonate. For this purpose, the circuitry 148 includes a differential amplifier 160 having first and said second input terminals 162 and 164, an output terminal 166 of the internal ground terminal 168. The output terminals of the respective pH electrodes 92 and 92' of the $CO_2$ sensors are connected to the respective first and second input terminals of differential amplifier 160. The internal ground terminal of the differential amplifier is connected by conductor 152 to the electrolyte ground connection 150 of the bicarbonate reagent. The differential amplifier thus provides at its output terminal a differential pH signal representing the pH differnce between pH electrodes 92 and 92'.

The output terminal of differential amplifier 160 is connected to a differentiator circuit 170 which is, in turn, connected to a peak pick and hold amplifier 172. The differentiator circuit differentiates the differential pH signal from amplfier 170 to derive a signal at its output proportional to the instantaneous time rate of change of pH. Amplifier 172 senses a maximum value of the time rate of change signal and provides an output at this maximum level. Recording means, such as a digital voltmeter 174, is connected between ground and a movable arm of potentiometer resistor 176 to display an output indicating carbon dioxide content in milli-equivalents per liter. The differentiator and amplifier circuits 170 and 172 may take the form illustrated and described in "Glucose Analyzer Service Manual, Beckman Instruction 83544-B," copyright 1970 by Beckman Instruments, Inc.

In practice, ten microliter samples are introduced into one milliliter of acid reagent in the analysis chamber 12.

When the sample is injected into the reagent in the chamber 12, carbon dioxide is instantaneously released and $CO_2$ measuring sensor 30 is directly exposed to and measures a proportion of this carbon dioxide. The carbon dioxide diffuses through membrane 108 and lowers the pH of the alkaline reagent in the electrolyte space 112 of the measuring sensor, and thus at pH electrode 92. Maximum rate of change of pH has been found to provide a measure of the carbon dioxide content in the sample. Typically, this maximum signal is derived and displayed directly in milliequivalents per liter by meter 174 in 20 seconds or less. Before injecting the next sample, the reaction chamber is drained and refilled with fresh reagent. Significantly, fresh electrolyte is pumped through measuring sensors 30 and 30' to prepare the sensors for the next measurement. Replenishing the electrolyte in this manner eliminates the long equilibration times associated with conventional carbon dioxide electrodes. Using a second pH electrode (electrode 92') eliminates inaccuracies introduced by junction potentials normally associated with conventional liquid-junction type reference electrodes. Moreover, there is no need to periodically replenish reference electrolyte of the liquid-junction type electrodes. It is apparent that the absolute pH of the alkaline electrolyte employed in the invention is not of interest and that exposing the pH electrode 92' to the alkaline electrolyte at a point remote from the electrolyte-carbon dioxide reaction in the measuring sensor 30 provides a differential pH signal between the two pH electrodes 92 and 92'. Coupling the measuring electrodes to respective input terminals of a differential amplifier provides extremely effective compensation for extraneous signals (common mode rejection) providing an enhanced signal-to-noise ratio with resulting improved sensitivity and precision of measurement. Coupling the solution ground 150 to the internal ground terminal of the differential amplifier insures that solution ground variations cancel out. The solution 150 may be relatively inexpensive metal connection in the electrolyte flow path.

The invention further includes apparatus for measuring the chloride content of the sample simultaneously with carbon dioxide content measurement. For this purpose, referring to FIGS. 3 and 5, the pair of electrodes 58, one of which is platinum and the other of which is silver, are coupled to a coulometric current generator for generating silver ions within the reaction chamber 12. In practice it is desirable to make the silver electrode of this pair relatively large and easily replaceable, since it is consumed during the titration and it may be located separately from the platinum electrode of 58 and the silver amperometric electrode pair 60. The pair of electrodes 60, both of which are silver, are connected to a differntial amplifier for monitoring the silver ions in the chamber and providing amperometric end point detection of the silver reaction. Differential amplifier 182 is in turn connected to current generator 180 by a conductor 184 is for controlling current generation. A current integrator 186 is connected to the platinum electrode of electrode pair 58 in order to measure the amount of charge passed between these electrodes. Digital voltmeter 188 is connected between the sliding arm of a potentiometer of resistance leg 188 and ground.

Detection of chloride in the sample is based upon the titration of the chloride with silver ions generated coulometrically. At the anode of the pair of detector electrodes 60 the following reaction is always available:

At the cathode, the following reaction is available only when excess silver ions are present:

When sample containing chloride is present, the small free silver ion concentration is no longer present due to precipitation as silver chloride. This condition, sensed by differential amplifier 182, is used to turn on current generator 180 causing the following reactions:

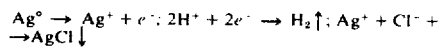

When all of the chloride in the sample has been precipitated by the generated silver ions, excess silver ions are produced, which results in a detector signal from amplifier 182 which turns off current generator 184.

A measure of the amount of charge required to titrate the chloride present is provided by the voltage output of current integrator 186. Digital voltmeter 188 directly converts this voltage output to a value calibrated in milliequivalents per liter of chloride.

Use of current integrator 186 in this manner eliminates the need to provide a constant current output for a prescribed time period as is the usual practice in coulometric chloride determination. In this manner, the actual current generated is integrated and fluctuations in this current signal are of no consequence.

Figure 6:
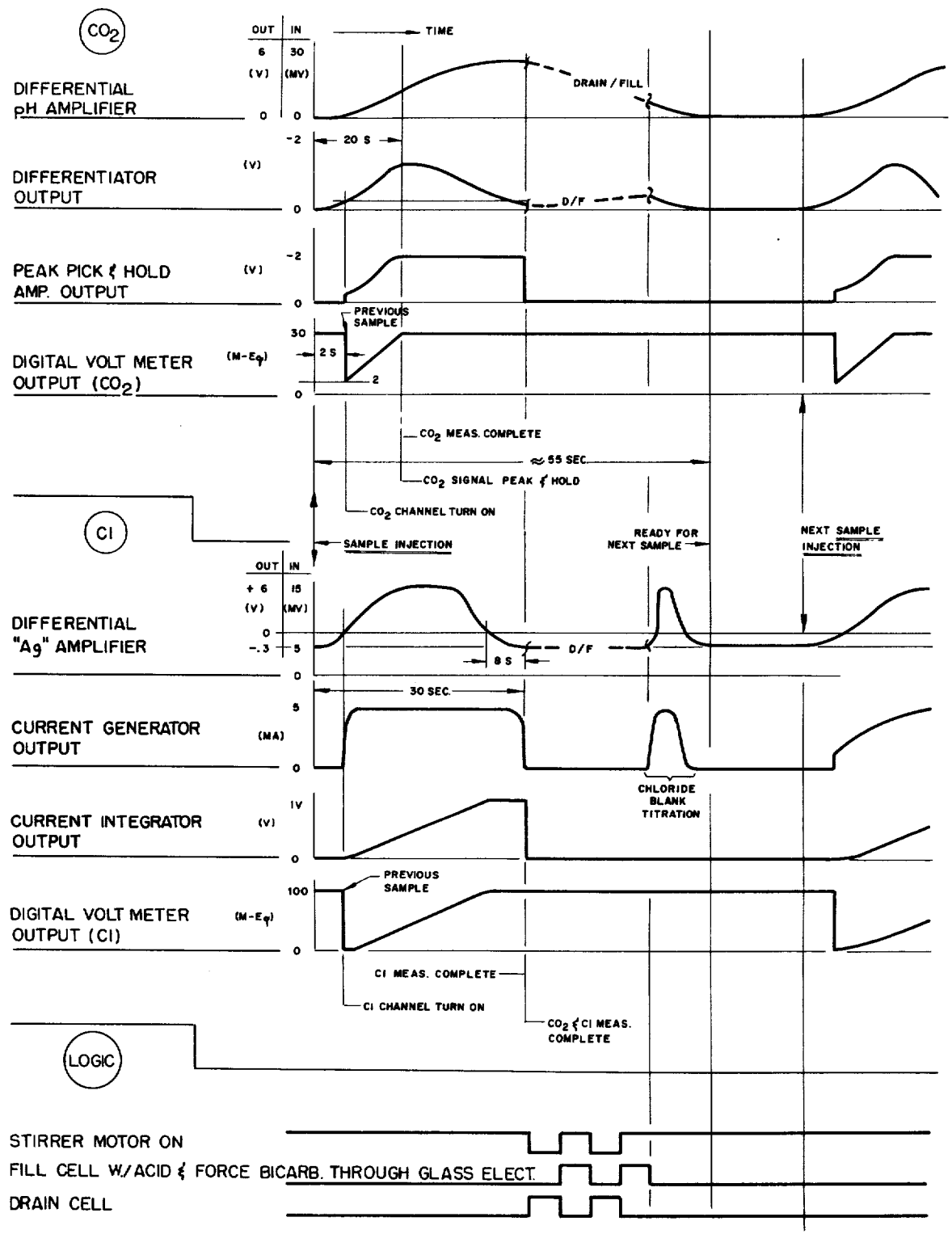
FIG. 6 is a graphic representation with respect to time of various electrical signals and logic commands derived in the operation of the apparatus of FIG. 5.

Typical waveforms for the operation of the analysis apparatus of the invention are illustrated in FIG. 6. In the figure time is depicted on the horizontal axis while various units of measure of the signals are illustrated on the vertical axis. The zero starting point is at the time of sample injection. The upper portion of FIG. 6 shows the waveform derived from the differential pH amplifier 160, differentiator circuit 170, the peak and hold amplifier 172, and the digital voltmeter 174. The various waveforms have been correspondingly labeled. The middle portion of the figure shows the waveform derived from the differential silver amplifier 182, the current generator 180, the current integrator 186, and the digital voltmeter 188. The waveforms are correspondingly labeled. The bottom of the figure shows the on-off condition for the stirrer motor, the filling of reaction chamber 12 with acid reagent and the circulating of bicarbonate electrolyte through the $CO_2$ sensors, and the draining of the reaction chamber.

As the carbon dioxide in the reaction chamber passes through membrane 108 into the $CO_2$ measuring sensor 30 and reacts with the electrolyte therein, a differential pH signal increases with time and the maximum rate of change of the signal is seen to occur at approximately 20 seconds after injection. The peak and hold amplifier holds this maximum level and the digital voltmeter displays the carbon dioxide concentration in milliequivalents per liter.

In the titration of chloride after sample injection, the signal at differential amplifier 182 turns on current generator 180 to generate silver ions, and the measure of the current is shown as the integrated waveform. The digital voltmeter provides a measure of the integrated current generated, and thus of the chloride titrated, and holds the measured value. The chloride titration is completed in 30 seconds or less.

In order to prepare the apparatus for the next injection, the $CO_2$ measuring sensors 30 and 30' and the reaction chamber 12 are drained and filled twice with appropriate reagents to insure that all residual reactants from the previous measurement are purged from the system. After the reaction chamber is filled with fresh reagent, a chloride blank titration is performed to precipitate out any chloride present in the reagent, so that upon injection of sample only the sample chloride will be measured.

In order to increase the sensitivity of the pH sensor 92, the waste conduit 144 from outlet tube 120 is connected to a constant pressure reservoir to maintain the pressure on membrane 108 constant. This is accomplished by positioning the outlet end of conduit 144 approximately 4 inches below the membrane to maintain the negative pressure differential across the membrane constant.

While the apparatus and method of the invention have been applied primarily to the measurement of carbon dioxide, it should be understood that they are equally applicable to the measurement of other acid gases, such as sulfur dioxide, oxides of nitrogen, or hydrogen cyanide, or to the measurement of other basic gases, such as ammonia or volatile amines. Moreover, while a preferred embodiment of the invention had been illustrated and described, it will be understood that various modifications may be made therein without departing from the spirit and scope of the invention as defined in the appended claims.

What is claimed is:
1. In combination:
   sensor means for monitoring a chemically reactable substance, said sensor means including an electrolyte which undergoes a chance in pH with time upon reaction with said substance,
   means coupled to said sensor means for generating an output signal proportional to the instantaneous time rate of change of pH of said electrolyte; and
   means for measuring said output signal to determine the concentration of said substance in said electrolyte.

2. The combination of claim 1 wherein said means for measuring includes means for measuring a maximum value of said output signal.

3. The combination of claim 1 wherein said sensor means includes means for producing a first signal proportional to the pH of said electrolyte and said generating means includes means for differentiating said first signal.

4. The combination of claim 1 wherein said sensor means includes:
   a pH measuring electrode having a sensing portion;
   means defining an electrolyte space communicating with the sensing portion of said measuring electrode for receiving an electrolyte which undergoes a change in pH upon reaction with said substance;
   a second electrode having a portion for communicating with an electrolyte;
   means for providing electrolyte communication between the electrolyte space of said measuring electrode and said portion of said second electrode; and
   said second electrode being positioned sufficiently remote from said measuring electrode whereby said substance reacts with electrolyte in the electrolyte space proximate said measuring electrode but does not react with the electrolyte proximate said second electrode to thereby provide a differential pH change between said measuring electrode and said second electrode.

5. The combination of claim 4 wherein said means for generating comprises:
   a differential amplifier having first and second input terminals and an output terminal;
   means for connecting electrical output terminals of said measuring and second electrode, respectively, to the first and second input terminals of said differential amplifier;
   differentiator means; and
   means connecting the output terminal of said differential amplifier to said differentiator means to generate said output signal.

6. The combination of claim 4 wherein said measuring electrode and said second electrode are both pH measuring electrodes.

7. The combination of claim 4 including means for periodically renewing said electrolyte comprising:
   an electrolyte reservoir;
   mean for supplying electrolyte from said reservoir to said measuring electrode and said second electrode including electrolyte inlet and outlet passage communicating with the electrolyte space of said measuring electrode, and inlet and outlet passages being positioned to direct flow through said electrolyte space to completely flush same and refill with electrolyte to rapidly equilibrate said measuring electrode.

8. The combination of claim 7 wherein said inlet and outlet passages are positioned on opposite sides of said electrolyte space.

9. The combination of claim 7 including means defining an electrolyte space adjacent said second electrode having electrolyte inlet and outlet passages, and wherein
   said electrolyte supply means together with said electrolyte communication means provides an electrolyte flow path from said electrolyte reservoir to a first waste reservoir through the electrolyte space of each of said measuring electrode and said second electrode.

10. The combination of claim 9 wherein said second electrode is situated in said electrolyte flow path upstream of said measuring electrode.

11. The combination of claim 10 wherein said electrolyte supply means includes first pump means for withdrawing a measured amount of electrolyte from said electrolyte reservoir and for delivering said measured electrolyte along said electrolyte flow path.

12. The combination of claim 9 including a reaction container for supporting a chemical reaction therein between a sample and a reagent, said sample containing a component of reaction so related to said substance that said means for measuring said output signal determines the concentration of said component;
   said measuring electrode being mounted in said container with the sensing portion thereof communicating with said chemical reaction through barrier means for passing said substance into the electrolyte space of said measuring electrode to the exclusion of unwanted components or products of said chemical reaction.

13. The combination of claim 12 including means for supplying reagent to said container from a reagent reservoir and means for discharging products of said chemical reaction therefrom to a second waste reservoir separate from said first waste reservoir.

14. The combination of claim 13 wherein said reagent supplying means includes pump means for withdrawing a measured amount of reagent from said reagent reservoir and for delivering said measured reagent to said container and said discharging means includes pump means for withdrawing said product of said chemical reaction from said container and for delivering same to said second waste reservoir.

15. The combination of claim 9 wherein said measuring electrode and said second electrode are both pH measuring electrodes each having means adjacent a sensing end thereof to define an electrolyte film space at each sensing end and said sample container includes a body of material defining a reaction chamber and having a first bore therethrough communicating with said reaction chamber for supporting said first measuring electrode with the sensing end thereof communicating with said reaction chamber and a blind bore therein for supporting said second measuring electrode.

16. An analytical method for measuring a substance by reacting said substance with an electrolyte comprising the steps of:

monitoring the pH of said electrolyte and generating an output signal proportional to the instantaneous time rate of change of the pH of said electrolyte upon reaction with said substance; and measuring said output signal to determine the concentration of said substance.

17. The method of claim 16 wherein said generating step includes generating a first signal proportional to the pH of said electrolyte and differentiating said first signal to derive said output signal.

18. The method of claim 17 wherein said step of measuring includes measuring a maximum of said output signal.

19. Th method of claim 17 wherein said step of generating a first signal includes monitoring the pH of said electrolyte at a first location where said electrolyte reacts with said substance and undergoes a resulting change in pH, monitoring the pH of said electrolyte at a second location remote from said reaction, and generating said first signal as a differential pH signal between said first and second locations.

20. The method of claim 16 comprising the step of reacting a sample and a reagent to derive said substance as a product thereof, said sample containing a component of reaction so related to said substance that said measuring of said output signal determines the concentration of said component.

21. An analytical method for analyzing a blood sample for bicarbonate and chloride including the steps of:

reacting said sample with a reagent in a container means to release carbon dioxide therefrom;

reacting said carbon dioxide with an electrolyte which undergoes a change in pH upon reaction therewith;

monitoring the pH of said electrolyte and generating an output signal proportional to the instantaneous time rate of change of said pH;

measuring said output signal to determine carbon dioxide concentration; and simultaneously coulometrically titrating said sample in said container means with silver ions to measure the chloride therein.

* * * * *